(12) United States Patent
Piluso et al.

(10) Patent No.: US 12,370,265 B2
(45) Date of Patent: Jul. 29, 2025

(54) HYDROGEL FOR IN-VIVO RELEASE OF MEDICATION

(71) Applicants: UMC Utrecht Holding B.V., Utrecht (NL); SentryX B.V., Austerlitz (NL); BO-IP B.V., Zeist (NL)

(72) Inventors: Susanna Piluso, Utrecht (NL); Jasper Gerard Steverink, Austerlitz (NL); Joannes Jacobus Verlaan, Utrecht (NL); Bas Jeroen Oosterman, Austerlitz (NL)

(73) Assignees: UMC Utrecht Holding B.V., Utrecht (NL); SentryX B.V., Utrecht (NL); BO-IP B.V., Zeist (NL)

( * ) Notice: Subject to any disclaimer, the term of this patent is extended or adjusted under 35 U.S.C. 154(b) by 704 days.

(21) Appl. No.: 17/611,659

(22) PCT Filed: Jun. 11, 2020

(86) PCT No.: PCT/EP2020/066238
§ 371 (c)(1),
(2) Date: Nov. 16, 2021

(87) PCT Pub. No.: WO2020/249695
PCT Pub. Date: Dec. 17, 2020

(65) Prior Publication Data
US 2022/0193254 A1    Jun. 23, 2022

(30) Foreign Application Priority Data

Jun. 11, 2019  (NL) ........................................ 2023291
Jun. 11, 2019  (WO) ................. PCT/NL2019/050352

(51) Int. Cl.
*A61K 47/69*   (2017.01)
*A61K 31/445*  (2006.01)
*A61K 45/06*   (2006.01)
*A61K 47/61*   (2017.01)

(52) U.S. Cl.
CPC ........ *A61K 47/6903* (2017.08); *A61K 31/445* (2013.01); *A61K 45/06* (2013.01); *A61K 47/61* (2017.08); *A61K 47/6915* (2017.08); *A61K 47/6951* (2017.08)

(58) Field of Classification Search
CPC ................ A61K 47/6903; A61K 47/61; A61K 47/6951; A61K 47/6915; A61K 31/445; A61K 45/06
See application file for complete search history.

(56) References Cited

U.S. PATENT DOCUMENTS

| | | |
|---|---|---|
| 2012/0040397 A1 | 2/2012 | Luo et al. |
| 2012/0321585 A1* | 12/2012 | Griffith ................ C08K 5/0025 530/356 |
| 2018/0355127 A1* | 12/2018 | Lim ......................... C08K 5/56 |
| 2019/0314556 A1 | 10/2019 | Lee et al. |

FOREIGN PATENT DOCUMENTS

| | | |
|---|---|---|
| NL | 2020071 B1 | 6/2019 |
| NL | 2023208 B1 | 12/2020 |
| WO | 2018/080221 A1 | 5/2018 |
| WO | 2019/002369 A1 | 1/2019 |
| WO | 2019/117715 A1 | 6/2019 |

OTHER PUBLICATIONS

Applegate, Matthew B. et al., "Photocrosslinking of Silk Fibroin Using Riboflavin for Ocular Prostheses", Advanced Materials, vol. 28, Issue 12, 2016, pp. 2417-2420.
Hoare, Todd R. et al., "Hydrogels in drug delivery: Progress and challenges", Polymer, vol. 49, No. 8, Apr. 1, 2008 (Apr. 1, 2008), pp. 1993-2007.
Qian, Feng et al., "Mechanically resilient, injectable, and bioadhesive supramolecular gelatin hydrogels crosslinked by weak host-guest interactions assist cell infiltration and in situ tissue regeneration", Biomaterials, Elsevier Science Publishers BV., Barking, GB, vol. 101, Jun. 2, 2016 (Jun. 2, 2016), pp. 217-228.
Qian, Feng et al., "Supporting Information—Mechanically Resilient, Injectable, and Bioadhesive Supramolecular Gelatin Hydrogels Crosslinked by Weak Host-Guest Interactions Assist Cell Infiltration and In Situ Tissue Regeneration", Jun. 2, 2016 (Jun. 2, 2016), Retrieved from the Internet: URL:https://ars.els-cdn.com/content/image/1-s2.0-S0142961216302289-mmc1.docx.
Thi, Thai Thanh Hoang et al., "Oxidized cyclodextrin-functionalized injectable gelatin hydrogels as a new platform for issue-adhesive hydrophobic drug delivery", RSC Advances, vol. 7, No. 54, Jan. 1, 2017 (Jan. 1, 2017), pp. 34053-34062.
Rodell, Christopher B. et al., "Supramolecular Guest-Host Interactions for the Preparation of Biomedical Materials", Bioconjugate Chemistry, ACS Publication, 2015 American Chemical Society, pp. 2279-2289.

* cited by examiner

*Primary Examiner* — Doan T Phan
(74) *Attorney, Agent, or Firm* — Hoffmann & Baron, LLP (57) ABSTRACT

A hydrogel for in-vivo release of medication includes at least one medication, where the hydrogel includes (i) a protein-based biopolymer functionalized with a functionalisation agent that is able to form guest-host interactions with oxidized β-cyclodextrin, preferably a primary aminoalkylphenol, more preferably gelatin functionalized with tyramine (GTA) and (ii) oxidized β-cyclodextrin (oβ-CD), where the hydrogel is cross-linked via exposure to visible light in presence of a biocompatible photoinitiator, resulting in a degree of swelling in the range of 2-20 calculated as (swollen weight−dry weight)/dry weight. It further relates to a method for its preparation, as well as to a medication for treatment of musculoskeletal disorders, preferably for treatment of infection, inflammation, malignant processes, growth disorders, degenerative disorders or treatment of pain arising from (surgical treatment of) these disorders.

20 Claims, 11 Drawing Sheets

HYDROGEL FOR IN-VIVO RELEASE OF MEDICATION

CROSS-REFERENCE TO RELATED APPLICATIONS

This application is the National Stage of International Application No. PCT/EP2020/066238, filed Jun. 11, 2020, which claims the benefit of Netherlands Application No. 2023291, filed Jun. 11, 2019, and International Application No. PCT/NL2019/050352, filed Jun. 11, 2019, the contents of which is incorporated by reference herein.

TECHNICAL FIELD

The present invention relates to a hydrogel for in-vivo release of medication. In particular it concerns a controlled and local release of medication, e.g., bupivacaine and/or other local anaesthetics. More in particular, the present invention relates to a hydrogel for close contact to skeletal structures. The invention further relates to the method of its preparation, both in-vitro and in-vivo.

BACKGROUND ART

Hydrogels are three-dimensional, physically or chemically cross-linked networks of water-soluble polymers. Their hydrophilic nature, water content similar to living tissue and elasticity, make them excellent candidates for biomedical applications. There is therefore quite some prior art on biodegradable hydrogels that are designed to release medication in the (human or animal) body in a sustained way.

For instance, in the J. Adv. Res. 2017, 8, 217-233, a thorough review by E. A. Kamoun et al may be found on hydrogels and their medical application. As indicated in the introduction of this article, a further overview may be found in Eur. Polym. J. 2015, 65, 252-267 by E. Caló et al, "Biomedical applications of hydrogels: A review of patents and commercial products".

Q. Feng et al describes "Mechanically resilient, injectable, and bioadhesive supramolecular gelatin hydrogels crosslinked by weak host-guest interactions assist cell infiltration and in situ tissue regeneration" in Biomaterials 2016, 101, 217-228.

In RSC Adv., 2017, 7, 34053, T. T. H. Thi et al describe injectable hydrogels as a novel platform for the release of hydrophobic drugs. An additional Schiff base reaction was introduced into a phenol-phenol crosslinked gelatin hydrogel to increase adhesiveness. β-cyclodextrin possessing a hydrophobic cavity and oxidized to present aldehyde groups (hereinafter "oβ-CD") was grafted to the gelatin backbone via Schiff base reaction, with the cavity providing encapsulation for hydrophobic drugs. Simply blending gelatin-tyramine (hereinafter "GTA") and oβ-CD in the presence of horseradish peroxidase and hydrogen peroxide (hereinafter "HRP/$H_2O_2$") rapidly and controllably formed GTA-oβ-CD hydrogels in situ. The optimal composition of GTA-oβ-CD hydrogels was found to be 5 wt % GTA with 1 wt % oβ-CD. Their elastic modulus and degradation rate were 1.8- and 1.5-fold higher than those of GTA hydrogels owing to additional imine bonds. Hydrophobic drugs (e.g., dexamethasone and curcumin) could be dissolved homogeneously in GTA-oβ-CD matrices with greater loading efficiencies than in GTA matrices. An in vitro test of cell viability using human dermal fibroblasts demonstrated that GTA-oβ-CD hydrogels were cytocompatible. In summary, dual-functional injectable GTA-oβ-CD hydrogels can be used as a promising platform to improve tissue adhesion and hydrophobic drug delivery.

Important factors to consider during the design of these hydrogels include 1) duration of delivery, and 2) location of delivery with respect to its working mechanism. For example, for effective local pain relief it is essential that an anaesthetic is delivered and remains in situ for a period in close proximity to the origin of pain. The problem of sustained release is particularly challenging for small molecules, such as Bupivacaine (hereafter "Bupi").

Bupi is a very effective and relatively inexpensive local anaesthetic. However, the duration of its effect is limited to approx. 8 hours. Increasing the dose or concentration of conventional bupivacaine solutions to obtain prolonged durations of effect can lead to both systemic and local toxicity, cf., Gitman M, Barrington MJ "Local Anesthetic Systemic Toxicity: A Review of Recent Case Reports and Registries" in Regional Anesthesia & Pain Medicine 2018; 43:124-130. Cardio- and central nervous system toxicity are well-known systemic toxic effect of bupivacaine. It is therefore of interest to find a way of releasing Bupi locally and in a delayed fashion, whereby it may work longer and with a decreased incidence of local and systemic cytotoxicity compared to conventional bupivacaine applications such as local bolus injection.

Moreover, few hydrogels meet the stringent requirements for a clinical translation with respect to the preparation, application, mechanical property, and biocompatibility of the hydrogel. The present inventors set out to design a biocompatible, biodegradable hydrogel with controlled and sustained release of medication. Moreover, the inventors set out to design a hydrogel that is versatile and easy to produce on a large scale, is easy to cross-link and can be cross-linked in a controlled manner to produce a hydrogel that is both flexible and strong. In this regard it should be understood that the hydrogel must be both sufficiently flexible and strong as to allow it to be implanted and to withstand local circumstances and forces so as to stay at the location of implantation for sufficient time to release the medication and not break or otherwise be damaged. This means that the hydrogel can adapt to a shape of a surface of, for instance, a skeletal structure against which it is pressed, whereby intimate contact with the outer bone surface of the skeletal structure is achieved. In a similar manner it may be pressed onto the surface of other musculoskeletal tissues or a surgical implant. Typically this requires a hydrogel with an elastic/compressive modulus (Young's modulus) of between 100 and 600 kPa.

SUMMARY OF THE INVENTION

The present invention provides a hydrogel for in-vivo release of medication comprising at least one medication, wherein the hydrogel comprises
   (i) a biopolymer functionalized with a primary aminoalkylphenol, preferably gelatin functionalized with tyramine (GTA) and
   (ii) oxidized β-cyclodextrin (oβ-CD),
   wherein the hydrogel is cross-linked via exposure to visible light in presence of a biocompatible photoinitiator, resulting in a degree of swelling in the range of 2-20, preferably 2-6, calculated as (swollen weight−dry weight)/dry weight. The swollen weight is the equilibrium weight of the hydrogel in vivo. The swollen weight may be experimentally determined in vitro after 24 h of swelling (or when it reaches equilibrium) in a simulated body fluid such as PBS at body temperature, such as 37° C.

BRIEF DESCRIPTION OF THE DRAWINGS

FIG. 3a shows a top view of a ring element according to an embodiment of the invention, FIG. 3b shows a cross-section A-A of the ring element of FIG. 3.a.

DETAILED DESCRIPTION OF THE INVENTION

Hydrogels may be synthesized by cross-linking water-soluble polymers. Water-soluble polymers such as poly (acrylic acid), poly(vinyl alcohol), poly(vinylpyrrolidone), poly(ethylene glycol), polyacrylamide and polysaccharides (e.g. hyaluronic acid) are the most common systems used to form hydrogels. These water-soluble polymers are biocompatible and widely used in various pharmaceutical and biomedical applications. It was found that these common hydrogels may be used as carrier for Bupi, but lack important properties such as being flexible/deformable yet robust, being bio-compatible and biodegradable and allowing for extensive tuning of its properties. Interestingly, it was found that cross-linking of biopolymers, such as gelatin and similar polymers may provide an improved carrier.

Although there are many different hydrogels, the present invention focusses on medical hydrogels that are biocompatible and can be implanted and used in-vivo. Moreover, they must be biodegradable. Because the hydrogels comprise a biopolymer, i.e. a natural polymer produced by a living organism, they are biodegradable, i.e. can be decomposed naturally inside the human body.

Although the invention is described with particular reference to using gelatin, any water-soluble biocompatible biopolymer may be used that comprises amino and hydroxyl groups. For instance, protein-based and/or polysaccharide-based polymers may be used, such as, hyaluronic acid, chitosan, and cellulose. Preferably, the biopolymer is a protein-based polymer, such as e.g. elastin, silk, collagen, fibrin or gelatin. More preferably the protein-based biopolymer is silk, collagen, fibrin or gelatin. These polymers contain tyrosine groups that may be used for the riboflavin mediated crosslinking. Most preferably, the hydrogel is based on gelatin. The hydrogel may also comprise other biocompatible water-soluble synthetic or natural polymers. The other polymers may compose up to 50% by weight on the entire polymer content. Given its availability, biocompatibility and cost, the use of gelatin as sole polymer component is preferred.

The amount of oxidized β-cyclodextrin versus biopolymer, preferably gelatin, may vary within broad ranges. Preferably, the amount of oβ-CD may be from 0.1% to 10% by weight of the hydrogels, preferably in the range of 2% to 6% by weight of the hydrogel. Using a higher amount of oxidized β-cyclodextrin can interfere with the chemical crosslinking of gelatin, due to increasing interaction between the tyramine functional groups and the oxidized β-cyclodextrin cavity.

The biopolymer, preferably gelatin, is preferably functionalized with tyramine, 4-(2-amino-ethyl)phenol as functionalisation agent. In addition to or instead of tyramine, other primary aminoalkylphenols of the formula $NH_2$—R-PhOH and substituted versions thereof may be used. Tyramine is the most common used compound to introduce phenolic hydroxyl groups on the gelatin backbone via functionalization with gelatin carboxylic acid groups. Alternatively, phenolic hydroxyl groups can be introduced via reaction with gelatin amino groups using functionalisation agents such as hydroxyphenyl propionic acid. Of importance is the biocompatibility of the functionalisation agent and its possibility to form guest-host interactions with the cyclodextrin. Given its availability, biocompatibility and cost, the use of tyramine as sole agent to functionalize the biopolymer is preferred.

The extent of functionalization may vary within broad ranges. To ensure appropriate cross-linking it is preferable that between 5-50%, preferably 20-25% of the carboxylic groups in the gelatin are reacted with tyramine or similar functionalisation agent. A similar extent of functionalisation is needed if an alternative biopolymer is used.

The use of β-cyclodextrin in hydrogels is known. In the present invention, the β-cyclodextrin is oxidized. The oxidation of β-cyclodextrin is needed to enable the grafting to gelatin. The degree of oxidation may vary from 5-30%, preferably from 20-30% of the secondary hydroxyl groups. Oxidation results in the conversion of secondary hydroxyl groups in the molecule into aldehyde groups. The preferred oxidation degree allows for maximal grafting of oβ-CD on the gelatin backbone, while limiting the cytotoxic effects that may result from any unreacted aldehyde groups and ensuring sufficient solubility of oβ-CD in water.

Although hydrogels based on GTA and cyclodextrin are known, the present inventors found that existing hydrogels could be improved in terms of their physical and chemical properties. As a result, the new hydrogels of the present invention can be implanted and fixated to specific locations where medication, in particular to achieve pain relief, is required. This may be a hydrogel in the form of e.g. deformable body, whereby the hydrogel conforms to the shape of a skeletal structure or surgical implant to which it is fixated. The new hydrogels therefore release their content, e.g., a medication like Bupi, always at the appropriate location. Of relevance in this respect is that a particular cross-link density is achieved, resulting in a degree of swelling that is in the range of 2-20, preferably in the range of 2-6, calculated as swollen weight (at equilibrium swelling)–dry weight/dry weight. The cross-link density is achieved by using crosslinks of the types:

(a) phenol-phenol crosslinks in the biopolymer functionalized with a primary aminoalkylphenol or similar functionalisation agent, (b) Schiff-base crosslinks between amino groups present on the functionalized biopolymer and aldehyde groups of oβ-CD, and (c) guest-host interactions between phenol moieties of the functionalisation agent grafted on the biopolymer and the cavity of oβ-CD.

The present invention in particular provides excellent control and adjustability of the formation of the phenol-phenol crosslinks. As a result, hydrogels may be produced with a wide variety of ratios between the crosslink types (a), (b) and (c). Moreover, by attuning the crosslink density, also the elasticity can be varied. The relevance of this is discussed herein below, where the various embodiments of the hydrogels of the present invention are discussed.

The direction of release of medication can be further improved by partly covering the surface of the hydrogel with a coating. Having the implanted hydrogel affixed adjacent to the body part that is to be treated, and moreover with the uncovered surface of the hydrogel adjacent to the body part that is to be treated, release of medication in other directions is reduced or even avoided. This has the advantage of reduced-side effects and the possibility to work with lower concentrations of medication or, alternatively, with a longer working time due to a slower release of the regular amount of medication.

The coating may be composed of the material of the hydrogel, provided that it contains no medication and is sufficiently thick. Preferably, however, the coating is composed of a material that is less permeable to the medication than the material of the hydrogel itself. The coating may be flexible or shell-like. Similar to the hydrogel, the coating must be composed of biocompatible biopolymers. The biodegradability may be the same or prolonged compared to the hydrogel. Suitable materials include but are not limited to polycaprolactone (hereinafter "PCL"), poly(lactic-co-glycolic acid) (hereinafter "PLGA"), gelatin, or alginate.

Of significant importance is therefore the nature of the photoinitiator. Crosslinking systems for cross-links of type (a) are known in the art and based on $HRP/H_2O_2$. Achieving crosslinks by use of a combination of riboflavin, sodium persulfate (SPS) and visible light is new. Riboflavin, also known as vitamin B2, is naturally recurring in the body, is biocompatible and is currently used in clinical application for the crosslinking of corneal collagen (Belin, Michael W., et al. *Cornea* 2018, 37, 1218-1225). The exposure of riboflavin to visible light, in presence of SPS, generates reactive intermediates. With visible light, the portion of the electromagnetic spectrum that is visible to the human eye is meant. A typical human eye will respond to wavelengths from about 380 to about 740 or even 780 nanometers. In particular, the invention has been tested with wavelengths between 400 and 700 nanometers. Other useable photoinitiators would be ferrocene, and anthraquinone.

Moreover, the use of a photo-induced crosslinking provides for better control and adjustability than the $HRP/H_2O_2$ system known from the prior art. Preferably the riboflavin and SPS are used in a molar ratio of 1:5-20, preferably about 1:10 (riboflavin:SPS). For instance, riboflavin and SPS may be used at 0.1-10 mM for riboflavin and 1-100 mM for SPS. Preferably the riboflavin is flavin mononucleotide, which is the water-soluble form of riboflavin.

As discussed above, by varying the amount of biopolymer vs cyclodextrin; by varying the functionalization of the biopolymer, by varying the amount of oxidation of the cyclodextrin, and by varying the amount of photoinitiator, the crosslink density and therefore the degree of swelling as well as the modulus of elasticity may be attuned to the intended use as e.g., ring-shaped hydrogel, sleeve-shaped hydrogel, thumbnail-shaped hydrogel, wedge-shaped hydrogel (e.g. for osteotomy), or other suitably shaped hydrogel, such as a shape suitable for application between a plate and a bone. For implantation and ability to provide sustained release of medication the following properties are desired.

High crosslinking degree, leading to a mechanically robust hydrogel and slow degradation. Therefore, degradation has minimal impact on drug release;

Directional release of drugs toward the preferred location, e.g., by use of a coating, and Ability to adapt to a shape of a surface of a structure against which it is pressed, such as a skeletal structure or a surgical implant, whereby intimate contact with the structure is achieved.

Figure 1:
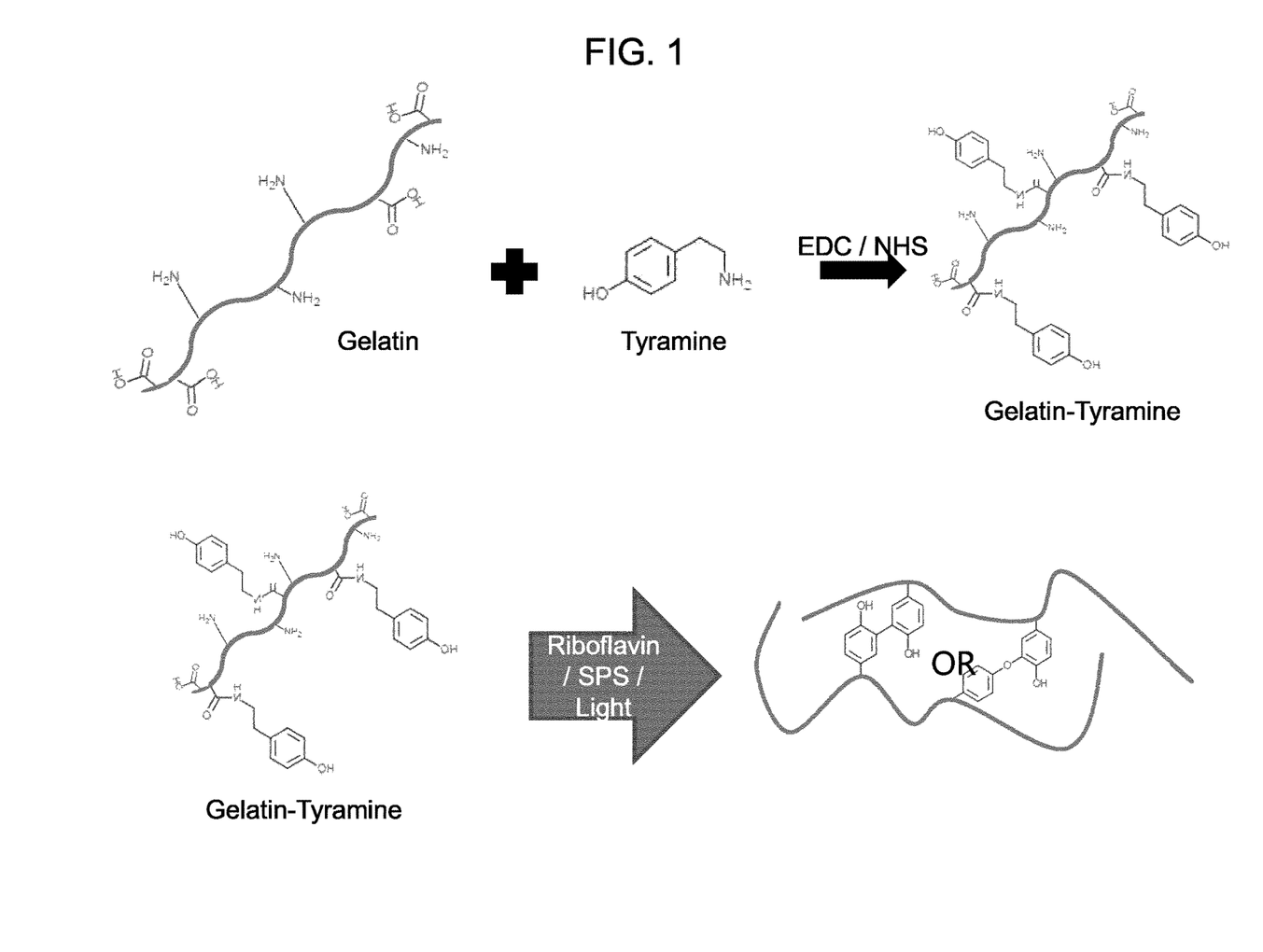
FIG. 1 is a schematic presentation of the formation of GTA and the crosslinking of GTA. Here the crosslinking of type (a) is shown under the influence of riboflavin/sodium persulfate (SPS) and light.
Figure 2:
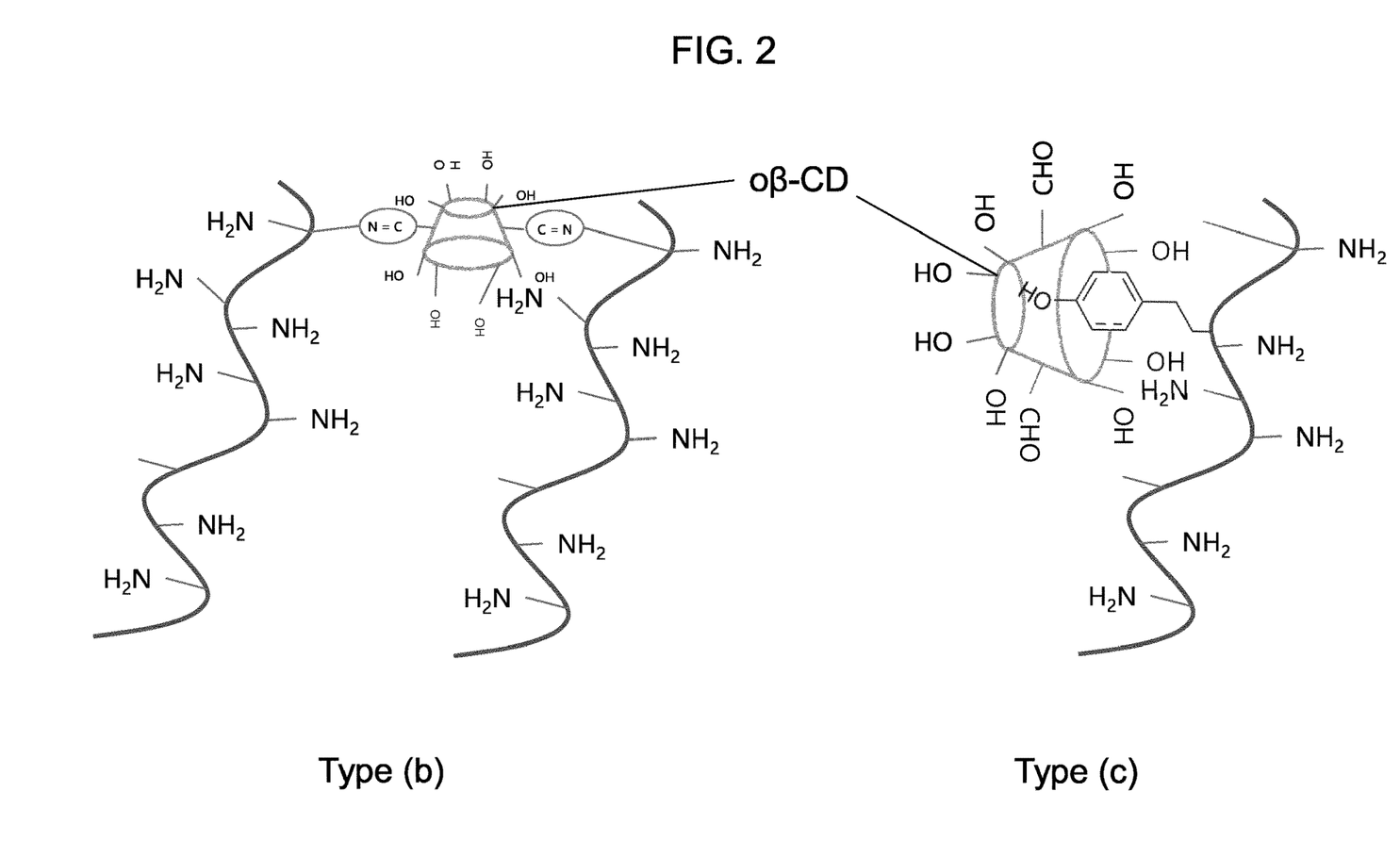
FIG. 2 is a schematic presentation of the crosslinking of type (b), amine groups of gelatin with aldehyde groups of oβ-CD in a Schiff reaction, and type (c) showing a guest-host interaction between the tyramine group of GTA and the cavity in cyclodextrin.
Figure 3:
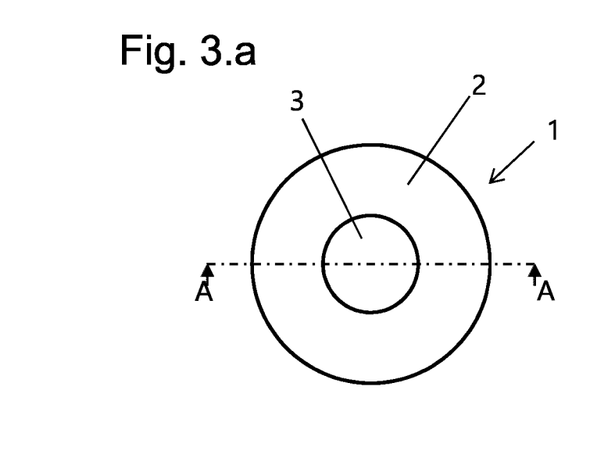
Figure 3B:
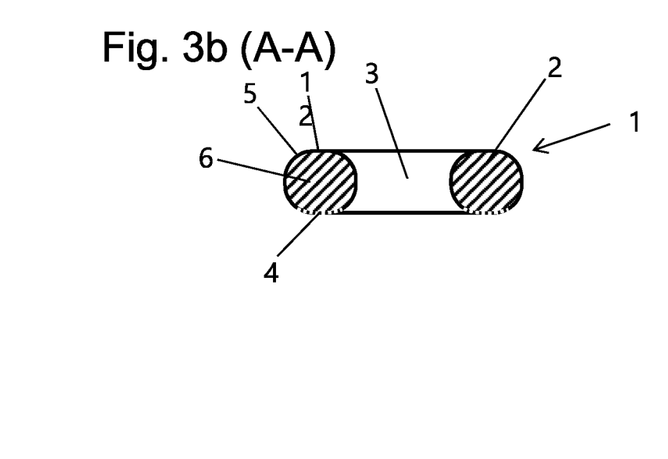
Figure 4:
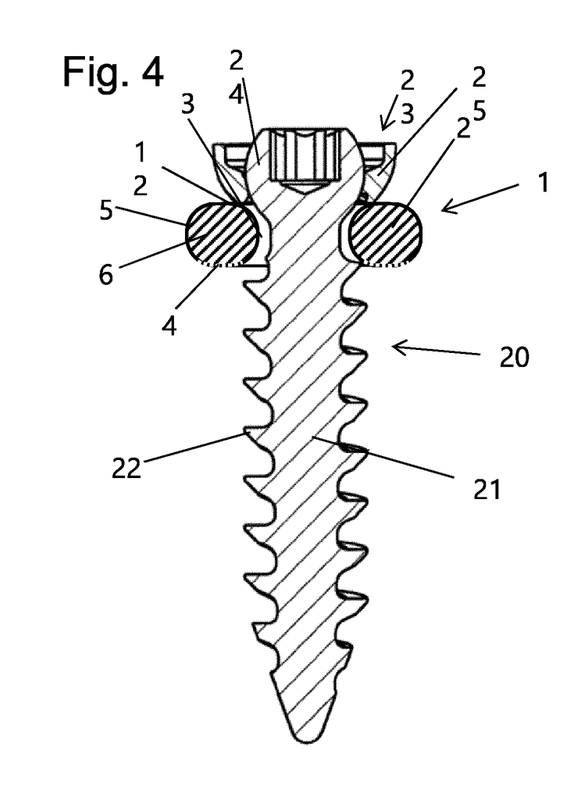
FIG. 4 shows a combination of a screw element and the ring element of FIG. 3a arranged on a shank of a screw element.

Turning to FIG. 3, the hydrogel may find different applications. In a co-pending application, the use of a hydrogel as carrier for local release of medication in the form of a ring is described (PCT/NL2018/050832, incorporated herein by reference) where it is used in combination with a screw. A hydrogel pursuant to the earlier invention is shown in FIG. 3*a*. FIG. 3*a* shows a top view of a ring element according to an embodiment of the invention, generally denoted by reference numeral 1. The ring element 1 comprises a deformable ring body 2 having a central opening 3. The ring element 1 is designed to be placed on a shank of a surgical screw element, for example a pedicle screw of a spinal fixation system. The ring body 2 is made of the hydrogel. FIG. 3*b* shows a cross-section A-A of the ring element 1. The outer surface wall of the ring element 1 is formed by a bone contact surface 4 and a compartment wall 5. The bone contact surface 4 and the compartment wall 5 delimit a compartment 6. The compartment 6, basically formed by the ring body 2 contains the medication. In a preferred embodiment, the bone contact surface 4 has, after implantation, a first release rate for the medication to be released and the compartment wall 5 has a second release rate for the medication to be released. Preferably, the first release rate is substantially larger than the second release rate, for example at least 2, preferably at least 10 times the second release rate. Pursuant to the preferred embodiment, the medication will be released from the compartment 6 mainly through the bone contact surface 4 according to a desired release profile over time. FIG. 4 shows a combination of a surgical screw element 20 and the ring element 1 of FIG. 3*a* mounted on a shank 21 of the screw element 20. The shank 21 comprises a screw thread 22 to screw the screw element 20 into a bore provided in a bone of a patient. The screw element 20 further comprises a proximal part 23 having a screw head 24 integral with the shank 21 and a separate connector part 25.

Figure 5:
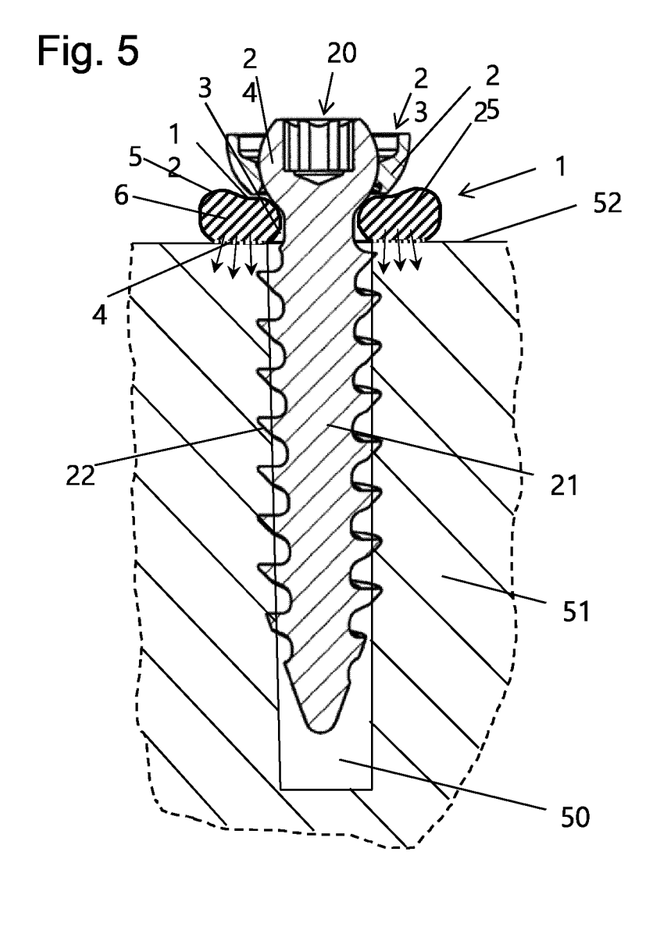
FIG. 5 shows the combination of FIG. 4 screwed into a bone of a patient.

It is remarked that the screw element 20 is a standard screw element, i.e. not specifically adapted for use in combination with the ring element 1. The screw element 20 is for example a screw element of the spinal fixation system disclosed in US 2010/031228. FIG. 5 shows the combination of the surgical screw element 20 and the ring element 1 after it has been screwed into a bore 50 provided in a bone 51 of a patient to be treated. The bone 51 is for example a pedicle of a spine of a patient. A hydrogel pursuant to the present invention, having a degree of swelling of approximately 4 and a modulus of elasticity of 400 kPa would be very suitable for said application.

Figure 6A:
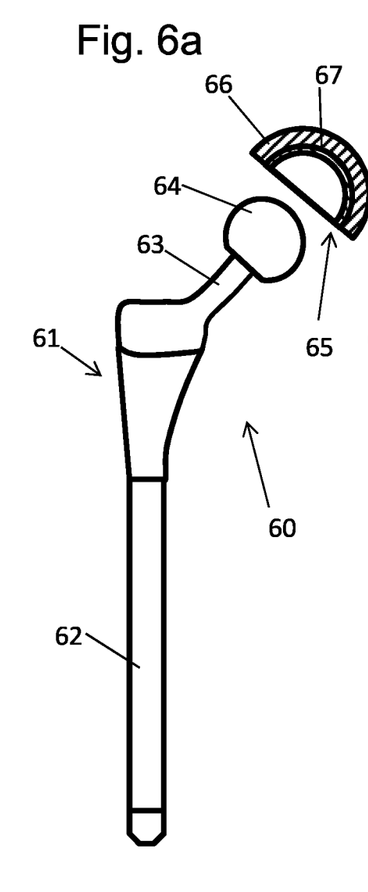
FIG. 6a shows an embodiment of a prosthetic hip implant.

In another co-pending application the use of a hydrogel as carrier for local release of medication in the form of a sleeve, e.g. for a joint prosthesis is described (NL2023208, incorporated herein by reference). A hydrogel pursuant to the earlier invention is shown in FIG. 6a. FIG. 6a shows a prosthetic hip implant generally denoted by reference numeral 60. The prosthetic hip implant 60 comprises a femoral component 61 to be connected to the femur of a patient and a acetabular component 65 to be connected to the acetabulum (hip socket) of a patient. The femoral component 61 comprises a stem 62 to be placed into the femur, a neck 63 and a head 64 supported on the neck 63. The acetabular component 65 comprises a acetabular cup 66 that may be provided with a liner 67 arranged in the acetabular cup 66. Prosthetic hip implants 60 are widely known in the art. Hip replacements using these types of prosthetic hip implants 60 is currently one of the most common orthopaedic operations, though patient satisfaction short- and long-term varies widely. In view of the possible negative effects of a hip replacement, such as pain and infection risks, there is a need to administer one or more medical active agents to the patient after implantation of the prosthetic hip implant 60.

Figure 6B:
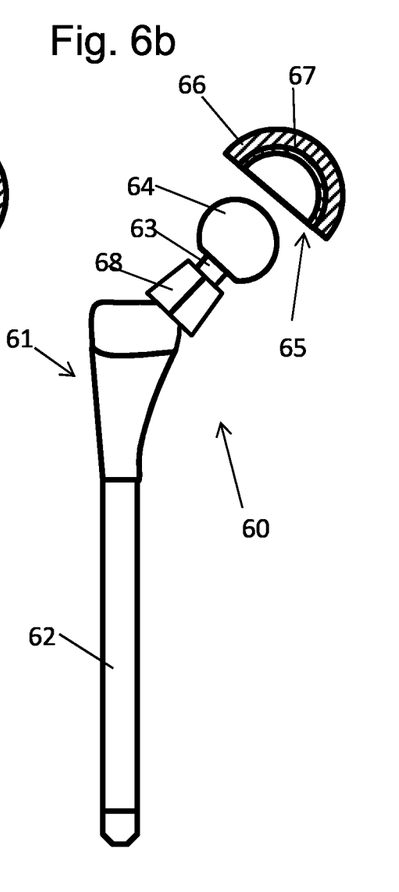
FIG. 6b shows the embodiment of the prosthetic hip implant of FIG. 6a including a first embodiment of a sleeve element arranged on the neck of the femoral component of the prosthetic hip implant.
Figure 7:
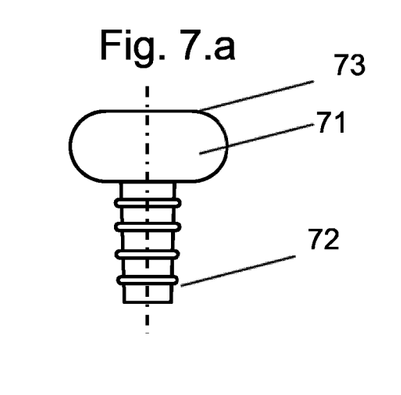
FIGS. 7a and 7b show an embodiment of a "thumbnail" with ring-like or screw like fastening means.
FIG. 7c shows the embodiment 7a arranged attached to a bone.

FIG. 6b shows the prosthetic hip implant 60 of FIG. 6a with a sleeve element 68 according to an embodiment of the invention arranged on the neck 63 of the femoral component 61. The sleeve element 68 comprises the hydrogel pursuant to the present invention and further comprising the medication, for example a pain treatment drug, such as an anaesthetic or analgesic. A hydrogel pursuant to the present invention, having a degree of swelling of approximately 4 and a modulus of elasticity of 400 kPa would be very suitable for said application.

In another application, the hydrogel is used as such, provided part of the hydrogel is rigid enough to act as pin of a "thumbnail", whereas the remainder of the hydrogel forms the head of the thumbnail. This is illustrated in FIG. 3c, where the pin is (72) and the head of the nail is (71). The medication may be contained in the shaft of the pin, or in the head of the nail. In this embodiment it is attractive to cover the outer surface of the head (73), away from the pin, with a coating of a biopolymer with a different permeability compared to the hydrogel. This ensured the directional release of the medication into the direction of the bone. A hydrogel pursuant to the present invention, having a degree of swelling of approximately 4 and a modulus of elasticity of 400 kPa would be very suitable for said application. Preferably, the head of the thumbnail is externally coated. Moreover, the pin may be made separately, from a biodegradable material other than a hydrogel.

Each of these embodiments is very suitable for treatment of musculoskeletal disorders, and especially for treatment of skeletal disorders due to the ability of the hydrogel to adapt to the shape of a bone or implant to which it has been pressed. These disorders include infection, inflammation, malignant processes, growth disorders, degenerative disorders, trauma, auto-immune diseases or treatment of pain arising from (surgical treatment of) these disorders. Preferably, these disorders include infection, inflammation, malignant processes, growth disorders, degenerative disorders or treatment of pain arising from (surgical treatment of) these disorders.

The present invention is described with reference to the use of Bupi, but any (local) anaesthetic may be used. Local anaesthetics are typically divided into amides and esters; amides are more commonly used. The anaesthetic is preferably an amino-amide local anaesthetic, such as articaine, procaine, chloroprocaine, etidocaine, prilocaine, bupivacaine, levobupivacaine, ropivacaine, mepivacaine, lidocaine, dibucaine, or other amino-caine, but may also be ester-based, such as tetracaine, procaine or chloroprocaine. The anaesthetic may also comprise a combination of two or more types of anaesthetics. Preferably, the anaesthetic is bupivacaine, liposome bupivacaine or levobupivacaine, lidocaine, or a combination of anaesthetics comprising bupivacaine, liposome bupivacaine and/or levobupivacaine. The medication may also be or comprise an antibiotic or anticancer agent, a growth factor, an immunomodulatory drug, etc. The medication may furthermore be hydrophilic or hydrophobic. Due to the hydrophilic nature of the hydrogel, a hydrophilic medication is easily incorporated into the hydrogel. The hydrophobic cavity of oβ-CD provides encapsulation for hydrophobic drugs. Therefore, with respect to hydrophobic medication, the hydrogel of the present invention has an advantage over hydrogels not comprising oβ-CD. Preferably, the medication is hydrophobic. A measure for the hydrophobicity of a medication is the octanol-water-partition coefficient P, which is the ratio of the concentrations of the medication in a mixture of octanol and water at equilibrium. For a hydrophobic medication log P>0, preferably log P>2.

The hydrogel may comprise additional components, like colorants, stabilizers, co-solvents, buffers and similar common additives. If and to the extent that bupivacaine is used as medication, it is preferably used in an amount of 0.01-200 mg/mL volume. Moreover, the medication may itself be encapsulated in nano- or microparticles, for instance, at a size range of 50 nm to 200 μm, prior to its inclusion in the hydrogel. It may be encapsulated in PLGA, PCL, gelatin, alginate or liposomes.

The release of bupivacaine from the hydrogel can be further extended by in situ crystallization of the drug. Specifically, the use of an alkaline solution as swelling medium for the hydrogel, induces the formation of bupivacaine crystals within the hydrogel matrix. The slow dissolution of the crystals in the surrounding medium enables the controlled release of bupivacaine.

In addition to the medication one or more further ingredients may be included, preferably further ingredients selected from co-medication, co-solvents, colorants, and buffers. Co-medication may be considered to be any further medication added to the hydrogel, preferably medication which enhances the effect of the at least one medication present in the hydrogel. Co-solvents include but are not limited to plasticizers. One such plasticizer is glycerol. The addition of glycerol into the hydrogel matrix results in higher elasticity, yet does not affect sample stiffness. The resulting hydrogels may have an elongation at break of between 100 and 300%, preferably of between 120 and 250%.

Methods for making the feedstock for the hydrogel are known. Thus, it is known to functionalize gelatin and related biopolymers with tyramine and related primary aminoalkylphenols. Likewise, it is known to oxidize cyclodextrin. See Thi et al, RSC Adv. 2017, which has been cited above, and which is included herein by reference. Of importance, but common in the field of medical application is to remove all forms of contamination. By way of example, the hydrogel may be prepared by the following method:

1. Solutions of GTA, oβ-CD, SPS, Riboflavin and bupivacaine are prepared.
2. Solutions are mixed so that pre-determined concentrations GTA, oβ-CD, SPS and Riboflavin are obtained. These concentrations can be varied depending on the desired mechanical and release properties, where higher GTA, oβ-CD (within a certain range) and SPS concentrations lead to a more densely cross-linked hydrogel.
3. The obtained solution is then exposed to visible light for a pre-determined amount of time. The time can be varied depending on the desired mechanical properties, where a low exposure time leads to a less densely cross-linked hydrogel.
4. The obtained hydrogel is then submerged in a bupivacaine solution to allow for diffusion of bupivacaine, and, if desired, co-solvents such as glycerol into the hydrogel.
5. The hydrogel is then dried and is ready for use.
6. Optionally, the hydrogel may be coated in part, e.g. with a solution of a biopolymer with a different permeability for bupivacaine compared to the hydrogel, to ensure directional release of the encapsulated medication. The coating may also enhance the mechanical properties of the hydrogel. The coating may be applied onto the hydrogel after step 6. Alternatively, it is also possible to form a shell of the coating in a pre-defined shape, and introduce the solution of step 2 into this shell, whereby the coating acts as a mould for the hydrogel.

By way of example, a coated hydrogel may be prepared as follows:

1. A solution of the biopolymer (e.g. PCL) in the appropriate solvent (in the case of PCL this is dichloromethane) is prepared. The PCL solution used ranges in concentration from 0.5-25 wt %.
2. Two options can be applied:
    a. A metal mould is dipped into the solution of biopolymer. The polymer solution coats the mould. The polymer solution is then left to dry and is removed from the mould. A coating in the shape of the mould has been constructed.
    b. The hydrogel is dipped into the solution of biopolymer. The solution coats the hydrogel. The polymer solution is then left to dry on the hydrogel to form a coating around the hydrogel. Using another method, the PCL solution can also be sprayed on the hydrogel, to achieve coating via spray coating.
3. Depending on the viscosity of the polymer solution, the duration of the dipping step, the speed of the dipping step (submersion and retraction) and the number of dipping repeats, e.g., between 1 and 10, a desired thickness of the coating can be obtained.
4. The coating then provides directional release, a slower release and degradation from/of the hydrogel due to a decreased diffusion surface and some mechanical support to the hydrogel.

Bupivacaine that is encapsulated in nano/microparticles may be added in step 2 to the solution, prior to step 3, exposure to light, thereby loading encapsulated bupivacaine into the hydrogel. In this case additional bupivacaine may be introduced into the hydrogel in step 4, but step 4 may be skipped as well.

Where in the above method gelatin functionalized with tyramine (GTA) is used, other biopolymers functionalized with a functionalization agent may be used, either instead of GTA or in addition to GTA. Likewise, where in the above method bupivacaine is used as medication, other medications may be used, as well as further ingredients selected from co-medication, co-solvents, colorants, and buffers.

This method may be used for hydrogels that are cross-linked outside the body wherein the hydrogel is used. As a modification of the above method, lacking step 6, it is also possible to mix the medication with solutions of GTA, oβ-CD, Riboflavin, SPS and bupivacaine and administer them into the body, for example by pouring or injection, at the location where the medication is to be applied. Step 3 is then performed in vivo.

EXAMPLES

The method described in the specification was applied.
Materials:
Gelatin (porcine skin, type A. 300 g bloom strength), 1-ethyl-3-(3-dimethylaminopropyl)-carbodiimide (EDC), N-hydroxysuccinimide (NHS), tyramine hydrochloride, 2-morpholinoethanesulfonic acid monohydrate (MES), sodium persulfate (SPS), sodium bicarbonate ($NaHCO_3$), sodium periodate, β-cyclodextrin, glycerol, phosphate-buffered saline (PBS), riboflavin (RB), and ethylene glycol were purchased from Sigma-Aldrich. Cellulose dialysis membranes (Spectra/Por™, 0.5 kDa; 12 kDa molecular weight cut-off) were purchased from Spectrum Laboratories. Bupivacaine was obtained from Siegfried, Switzerland.
Synthesis of Gelatin-Tyramine (GTA)
Gelatin type A was dissolved in MES buffer at 50° C. followed by addition of tyramine, EDC and NHS. The reaction mixture was left to react overnight with stirring. The mixture was then dialyzed against water and the product was obtained by lyophilization.
Tyramine Content Measurement
The degree of functionalization of gelatin was determined by measuring the absorbance of the polymer solution (0.1%, w/v) at 275 nm and calculated from a calibration curve obtained by measuring the absorbance of known percentages of tyramine in distilled water.
Oxidation of β-Cyclodextrin
Oxidized β-cyclodextrin was prepared by reaction with sodium periodate. Briefly, β-cyclodextrin was dispersed in distilled water followed by addition of sodium periodate and stirred at room temperature in the dark, overnight. The reaction was terminated by the addition of ethylene glycol. The mixture was dialyzed against deionized water using a dialysis membrane with an MWCO of 500 Da (Spectrum Labs) for 3 days and the product was collected by lyophilization. The degree of oxidation was determined by $^1H$ NMR, using either deuterated dimethyl sulfoxide (DMSO-d6) or deuterium oxide (D2O) as solvent. Whereas β-cyclodextrin has a ratio of protons at 4.8-4.9 ppm versus 4 ppm of about 2.04, progress of the reaction can be seen by a change in the ratio, to about 1.49.
Fabrication of GTA/β-Cyclodextrin Hydrogels
Prior to hydrogel crosslinking, solutions of GTA, oβ-CD, SPS and Riboflavin were prepared. Unless indicated otherwise, GTA had a degree of functionalization of 10-25%, whereas oβ-CD with an oxidation degree of the secondary hydroxyl groups of 15-30% was used. These solutions were mixed so that final concentrations of 20 wt % GTA, 0-10 wt % oβ-CD, 0-100 mM SPS and 0-10 mM Riboflavin were obtained. Samples without oβ-CD have been used as control. The obtained solution was exposed to visible light, in particular to visible light from a white-light lamp, using a wavelength range of 400-700 nm, to enable hydrogel formation.

Determination of Swelling Ratio:

Swelling studies were conducted on disc-shaped GTA hydrogels prepared by using custom-built molds. After synthesis, hydrogel samples were immersed in PBS at pH 7.4 and 37° C. for 24 h or until equilibrium swelling was achieved. At predetermined time points, excess water was removed and the samples weighed ($W_s$). The hydrogels were then lyophilized to obtain the dry weight (Wd). The swelling ratio was defined as $(W_s-W_d)/W_d$.

To determine the gel fraction, samples were freeze-dried ($W_{d1}$) after synthesis and then soaked in water for 24 h, to remove the soluble fraction. The hydrogels were then dried ($W_{d2}$) and the gel fraction (%) was calculated as $(W_{d1}/W_{d2}) \times 100\%$.

Crystallization

To induce the formation of bupivacaine crystals, after synthesis the hydrogels were soaked in a 0.1M NaHCO3 aqueous buffer (pH 8.5) (optionally comprising 30% (v/v) glycerol) for 2 h to induce drug crystallization (and optionally allow diffusion of glycerol) into the hydrogel. The hydrogels were then left to dry at 37° C.

Mechanical Testing:

Compression testing was performed on disc-shaped swollen hydrogels using a dynamic mechanical analyzer (DMA Q800, TA Instruments, UK). Experiments were conducted at room temperature in controlled force mode with a force ramp rate of 3N min$^{-1}$ up to 18 N. The elastic modulus was determined from the slope of the stress-strain curve at 5-10% strain.

The force needed to induce plastic deformation of the tested material (i.e. no return to original form/shape/state) was measured at room temperature using the Mark-10 ES10 manual force test stand with a maximum capacity of 500 N. A parallel-plate design was used with a cross-section of 1 cm on hydrogels of with a diameter of 5 mm. The compression force applied was measured with a digital force gauge incorporated in the Mark-10 ES10.

The elongation of the ring-shaped hydrogel was measured using a customized method, by mounting the sample on a caliper tool. The caliper was first used to measure the initial inner diameter of the ring, and then gradually extended. Inner diameter of the ring upon breaking was noted. The elongation was then calculated as ((ID upon breaking–ID resting state)/ID resting state)*100%.

Rheological Behavior:

To study the interaction between GT A and oβCD, rheology experiments were performed.

Rheology—Gelation Time

Immediately after mixing the solutions of functionalized gelatin and oβCD (final concentrations of 20% and 2% (w/v), respectively), the solution was deposited on the rheometer plate and the gelation was monitored over time (strain was set constant at 1% and angular frequency at 1 rad/s) at 37° C. At approximately 8 min a crossover between the storage modulus (G') and viscous modulus (G") was observed, with G' being higher than G", indicating the gelation point. Gelation was monitored for a total of 90 min, then the experiment was stopped. This experiment clearly confirms that in the final hydrogel, besides phenol-phenol coupling, there are also additional crosslinks (Schiff base reaction: host-guest interactions) between oβCD and modified polymer.

Rheology—Dynamic Amplitude Test (High Strain Deformation)

Figure 8:
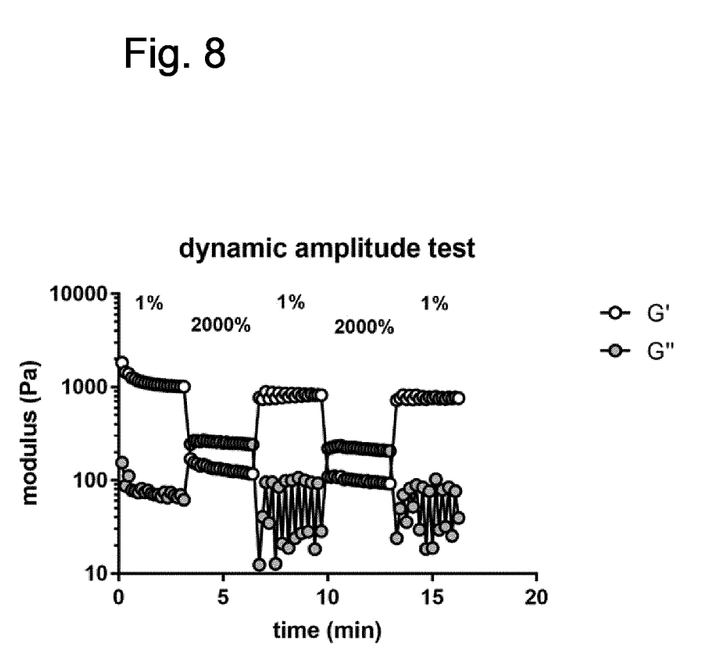
FIG. 8 shows a graph of dynamic amplitude testing of GTA-oβCD mixtures.

Following the gelation experiment, dynamic oscillatory amplitude test was performed to assess the reversibility of the crosslinking interactions in the network. Alternating cycles at low strain (1%) and high strain (2000%), at a constant angular frequency of 1 rad/s were applied and G' and G" were monitored. Each cycle was performed for 200 sec (FIG. 8). At low strain (1%). G' (open circles) is higher than G" (grey circles), indicating a solid-like behavior. Then, in the next cycle, strain was increased to 2000%, and G" was higher than G', indicating a viscous-like behavior. In a next step when the strain was reduced, the material was able to recover its original stiffness. This experiment shows the self-healing ability of the hydrogel material, due to the presence of interactions between oβCD and the tyramine-functionalized gelatin, acting as sacrificial bonds in addition to dityrosine crosslinks, contributing to increased mechanical properties of the hydrogel material.

Drug Loading and In Vitro Drug Release Assay

For the investigation of drug release properties, the obtained hydrogels were loaded with bupivacaine by immersion in an aqueous solution of bupivacaine at 50 mg/mL for 24 hours, followed by pH-induced crystallization of bupivacaine inside the matrix.

The release of bupivacaine from the hydrogels was measured by placing the hydrogels in a vial containing 1 mL of 0.1M citrate buffer, pH6 at 37° C.

At predetermined time points, aliquots of 100 uL samples were taken from the release solution and replaced with fresh buffer. The samples were diluted 1:10. Bupivacaine release was determined by UPLC using ammonium formate (10 mM, pH 2.4) and a mixture of acetonitrile/water/formic acid (96:5:0.2, v:v:v) as mobile phase.

Analytical Results

Swelling ratio and sol fraction of hydrogels with increasing concentrations of photoinitiator were analyzed. Swelling ratio was similar at all the concentrations tested; slightly above 4. The sol fraction (the non-crosslinked part of the gel) was lowest at the 2 mM concentration, close to 0%, with around 1% for the other hydrogels. 2 mM is the preferred concentration for hydrogel.

Figure 9:
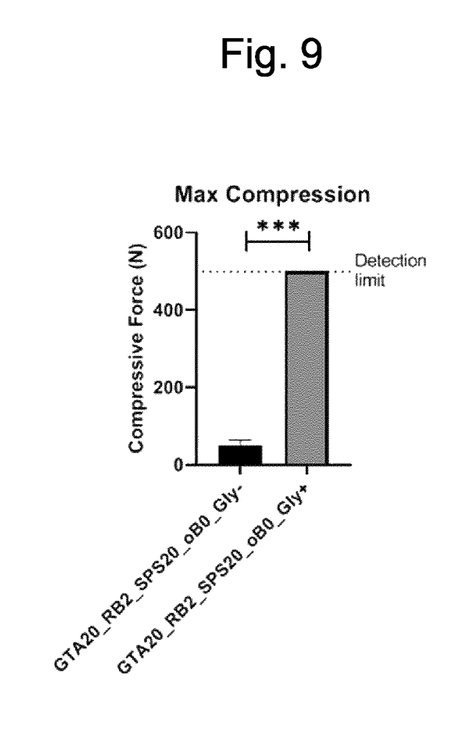
FIG. 9 shows a graph of the compressive force of hydrogels having a GTA content of 20 wt % before and after glycerol treatment.

Hydrogels (control) based on 10, 15 and 20 wt % GTA, and using riboflavin/SPS as photoinitiator were prepared, by exposure to visible light for a fixed time. Hydrogels having a GTA content of 20 wt % displayed maximum compressive force resistance of 52±13N. After glycerol treatment, the hydrogels with 10 wt % GTA content displayed a compressive force of between 200 and 400 N, and the hydrogel with a GTA content of 15% displayed a compressive force of greater than 400 N. The hydrogel with a GTA content of 20% was the most resistant to compression, scoring well above the 400 N (FIG. 9).

Figure 10:
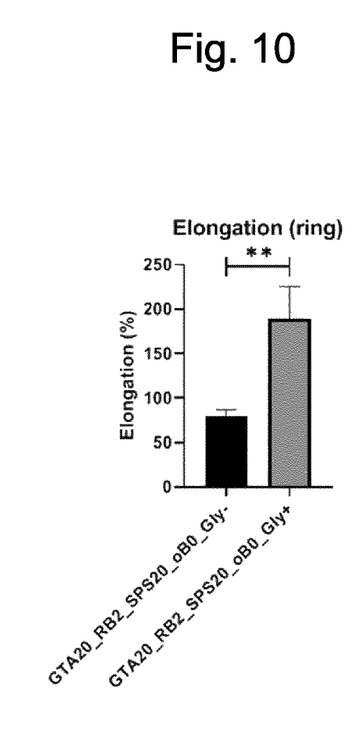
FIG. 10 shows a graph of the elongation at break (% of original inner diameter) of ring-shaped hydrogels having a GTA content of 20 wt % before and after glycerol treatment.

Furthermore, the addition of glycerol to the hydrogel matrix improved the elasticity, as the elongation significantly increased from 80.3±6.5% to 189.3±56.8% for ring-shaped hydrogels before and after glycerol treatment, respectively (FIG. 10).

Again, hydrogels (control) were made, but now with a fixed GTA content of 20 wt %, using increasing SPS concentrations, followed by exposure to visible light. At 0 mM SPS no hydrogel was formed. At low concentrations hydrogel did not retain its form. Higher concentrations of SPS led to hydrogels exceeding the maximum capacity of the mechanical tester (500 N). Based on the present invention, the concentration of SPS selected gave the optimal mechanical properties and lowest cytotoxic effect.

Again, hydrogels were made, but now with a fixed GTA content of 20 wt %, a fixed RB/SPS concentration and with different amounts of oβ-CD, 0 wt % (control), 2 wt % (invention), 4 wt % (invention) and 6 wt % (invention). Higher concentrations of oβ-CD lead to decreased swelling and therefore increased crosslinking. The swelling ratio varied from about 6 to 3.

Figure 11:
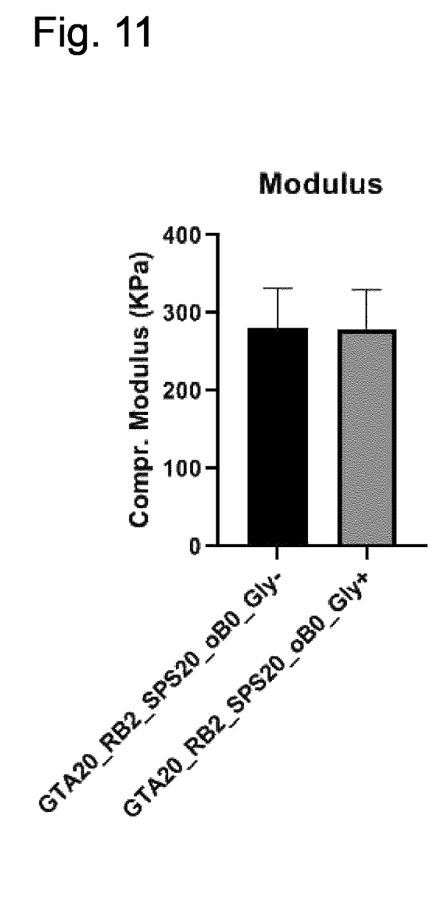
FIG. 11 shows a graph of the compressive modulus of GTA hydrogels at 20 wt %, before and after treatment with glycerol.

The effect of irradiation time on the compressive modulus was evaluated on hydrogels prepared with a GTA content of 20 wt %, a fixed ratio of RB/SPS and a fixed concentration of oβ-CD. Increasing the irradiation time led to increase of compressive modulus of the hydrogel. The compressive modulus was found to be from 167.5 (±20) kPa (5 min), from 328.3 (±29) kPa (10 min); from 455.7 (±63) kPa (20 min), and from 552.3 (±138) kPa (30 min). Increasing the irradiation time also led to decreased swelling of the hydrogels, consistent with the increased crosslinking. The swelling reached a value of about 4 for irradiation time between 10 and 30 min. The addition of glycerol to the hydrogels did not lead to changes in compressive modulus (FIG. 11).

Again, hydrogels were made with various concentrations of oβ-CD. The effect on the compressive modulus of incorporating bupivacaine into the hydrogels was tested. It was found to have no effect on the compressive modulus. As was determined before, increase of oβ-CD does increase the compressive modulus of hydrogels.

Hydrogels were made pursuant to Thi et al, RSC Adv. 2017, which has been cited above, with a GTA content of 20 wt %, HRP of 0.5 EU/mL, $H_2O_2$ 0.04%, and different concentrations of oβ-CD. These were compared with hydrogel made pursuant to the present invention, with a similar content of GTA and oβ-CD, but prepared with RB and SPS as photoinitiator. The hydrogels according to the present invention showed higher compressive moduli at the same polymer concentrations.

The cytotoxicity of separate components of the hydrogel of the present invention was tested using a Live/Dead assay using human MSC cells. Cells were exposed to the compound (dissolved in PBS) for 1 hour at the concentrations stated. Cell viability was compared to control wells, with hydrogels exposed to PBS only for 1 hour. Live/Dead assay was performed according to the manufacturer's protocol after 48 hours. Cell viability was similar to the control wells for all concentrations of riboflavin and oβ-CD tested.

The metabolic activity of human MSCs was assessed using an alamarBlue™ assay. Cells were exposed to either the hydrogels pursuant to Thi et al, RSC Adv. 2017, which has been cited above, or hydrogels pursuant to the present invention of equal GTA content for 48 hours. Subsequently, the assay was performed according to the protocol. The metabolic activity of the tested hydrogels was almost similar to the control, confirming the cytocompatibility of the present photoinitiator. No significant differences in cell viability or metabolic activity were observed in hydrogels before and after glycerol treatment.

Further, the use of an alkaline buffer to induce crystallization of bupivacaine within the hydrogel, did not lead to any cytotoxic effect when in contact with cells.

Figure 12:
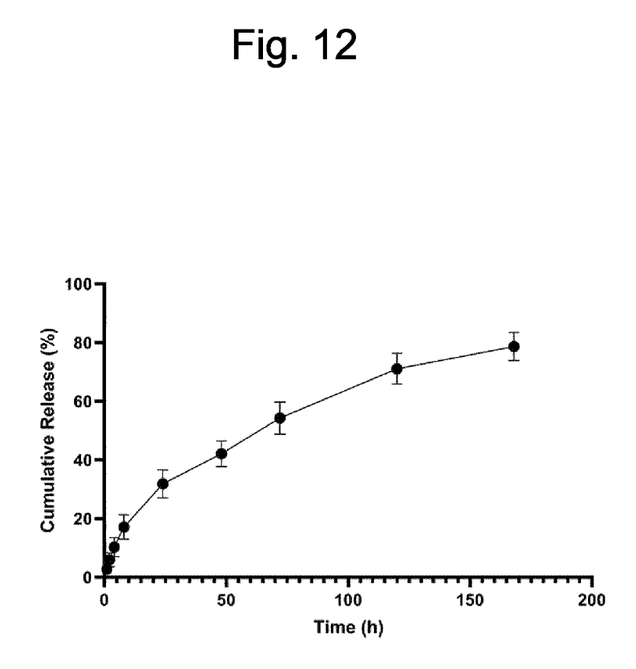
FIG. 12 shows a graph of the cumulative release of bupivacaine crystals from the hydrogel matrix in 0.01M citrate buffer pH 6. The hydrogel was partly coated with a PLGA film. Release is expressed as a percentage of total drug content.

Release of crystallized bupivacaine from the partially PLGA-coated hydrogel exceeded 168 h in 0.01 M citrate buffer pH 6.0. The release profile was characterized by an initial burst release (approx. 20% of total drug content in first 8 h), followed by a phase of near-linear release of bupivacaine. After 168 h of drug release, 20% of total drug content remained inside the hydrogel (FIG. 12) as determined following completion of the experiment by degradation of the hydrogel.

To determine the influence of a coating on directional release, a methylene-blue containing hydrogel was cast on a 180 μm-thick PCL film obtained by casting. Release of methylene blue from the hydrogel was simulated in a 3% alginate gel, cross-linked with calcium chloride to obtain a tissue-like consistency. Only the top part of the hydrogel was coated with PCL. The samples were inspected at 0, 1, 2, and 3 hours. Hydrogels were positioned vertically to eliminate any effect of gravity on the direction of release. Visual inspection revealed that methylene blue was released only in the non-PCL-covered direction. The same experiment was performed with bupivacaine. The cumulative release was assessed and found to reach about 2 mg after 8 hours from the PCL-covered direction, whereas in the non-PCL covered direction this was reached within 1 hour. This confirms that a coating may be used to provide directional release of the medication within the hydrogel.

The invention claimed is:

1. A hydrogel for in-vivo release of medication comprising at least one medication, wherein the hydrogel comprises
    (i) a protein based biopolymer functionalized with a functionalization agent that has introduced phenolic hydroxyl groups that are able to form guest-host interactions with oxidized β-cyclodextrin and
    (ii) oxidized β-cyclodextrin (oβ-CD),
    wherein the hydrogel is cross-linked via exposure to visible light in presence of a biocompatible photoinitiator, resulting in a degree of swelling in the range of 2% to 20%, and
    wherein the biocompatible photoinitiator is a combination of riboflavin and sodium persulfate.

2. The hydrogel of claim 1, further comprising a co-solvent.

3. The hydrogel of claim 2, wherein the plasticizer is glycerol.

4. The hydrogel of claim 1, wherein from 10% to 30% of the secondary hydroxyl groups within oβ-CD have been converted into aldehyde groups.

5. The hydrogel of claim 1, wherein the amount of oβ-CD is from 0.1% to 10% by weight of the hydrogel.

6. The hydrogel of claim 1, comprising bupivacaine as medication in an amount of 0.01-200 mg/mL volume.

7. The hydrogel of claim 1, wherein the medication is encapsulated in a biopolymer.

8. The hydrogel of claim 1, comprising bupivacaine as medication and one or more further ingredients.

9. The hydrogel of claim 1, comprising crosslinks of the types
    (a) phenol-phenol crosslinks in the biopolymer functionalized with the functionalization agent;
    (b) Schiff-base crosslinks between amino groups present on the functionalized biopolymer and aldehyde groups of oβ-CD; and
    (c) guest-host interactions between the phenol moieties of the primary aminoalkylphenol grafted on the biopolymer and the cavity of oβ-CD.

10. The hydrogel of claim 1, comprising a modulus of elasticity as measured from the slope of a stress-strain curve obtained by dynamic mechanical analysis in controlled force mode with a force ramp rate of 3 N $min^{-1}$ up to 18 N at 5-10% strain, that is between 100 and 600 kPa.

11. The hydrogel of claim 1, covered in part by a coating.

12. The hydrogel of claim 1, wherein the protein based biopolymer (i) is selected from silk, collagen, fibrin or gelatin.

13. The hydrogel of claim 1, wherein the functionalization agent is a primary aminoalkylphenol.

14. The hydrogel of claim 1, wherein the medication is a hydrophobic medication.

15. The hydrogel of claim 14, wherein the protein based biopolymer functionalized with a functionalization agent is gelatin functionalized with tyramine (GTA).

16. The hydrogel according to claim 1, having degree of swelling in the range of approximately 4 and a modulus of elasticity as measured from the slope of a stress-strain curve obtained by dynamic mechanical analysis in controlled force mode with a force ramp rate of 3 N $min^{-1}$ up to 18 N at 5-10% strain, that is approximately 400 kPa, and that
(a) is provided with a hole for attachment to a bone, or
(b) is shaped as a sleeve to encompass part of a bone, or
(c) Is shaped as a thumbnail and comprises a rigid part for fixation onto a bone.

17. The hydrogel according to claim 1, having an elongation at break of between 100% and 300%.

18. A method for preparing the hydrogel according to claim 1, the method comprising:
preparing a mixed solution of the protein based biopolymer functionalized with the functionalization agent, the oxidized β-cyclodextrin (oβ-CD), the biocompatible photoinitiator, and the medication of claim 1,
exposing the mixed solution to visible light to generate a hydrogel, and
drying the hydrogel,
wherein the hydrogel is cross-linked via exposure to the visible light in presence of the biocompatible photoinitiator, resulting in a degree of swelling in the range of 2% to 20%, and
wherein the biocompatible photoinitiator is a combination of riboflavin and sodium persulfate.

19. The hydrogel according to claim 1, for use in the treatment of musculoskeletal disorders, infection, inflammation, malignant processes, growth disorders, degenerative disorders, trauma, auto-immune diseases or treatment of pain arising from surgical treating of the disorders thereof.

20. The hydrogel according to claim 19, which is prepared in vivo by administering a combination of
(a) the protein biopolymer functionalized with functionalization agent mixed with the medication in liquid form or encapsulated in microparticles with
(b) a biopolymer functionalized with oβ-CD, and
wherein the combination is exposed to visible light in vivo, to generate the hydrogel in vivo.

\* \* \* \* \*